United States Patent [19]

Kitamura et al.

[11] 4,214,111

[45] Jul. 22, 1980

[54] METHOD OF PRODUCING OLEFIN OLIGOMERS AND HYDROGENATION PRODUCTS THEREOF

[75] Inventors: Takanori Kitamura; Masuhiko Tamura, both of Kurashiki, Japan

[73] Assignee: Kuraray Co., Ltd., Kurashiki, Japan

[21] Appl. No.: 958,144

[22] Filed: Nov. 6, 1978

[30] Foreign Application Priority Data

Nov. 8, 1977 [JP] Japan .................................. 52/134481
Sep. 4, 1978 [JP] Japan .................................. 53/108853

[51] Int. Cl.$^2$ ........................... C07C 3/18; C07C 5/04
[52] U.S. Cl. ..................................... 585/255; 585/329; 585/532
[58] Field of Search ................... 260/683.15 B, 676 R, 260/683.9; 585/329, 255, 532

[56] References Cited

U.S. PATENT DOCUMENTS

| | | | |
|---|---|---|---|
| 3,149,178 | 9/1964 | Hamilton et al. | 260/683.9 |
| 3,652,706 | 3/1972 | Saines et al. | 260/683.15 B |
| 3,957,664 | 5/1976 | Heilman et al. | 260/683.15 B |
| 3,985,822 | 10/1976 | Watson | 260/683.15 B |

*Primary Examiner*—C. Davis
*Attorney, Agent, or Firm*—Barry Kramer

[57] ABSTRACT

A method of producing liquid hydrocarbons useful e.g. as lubricants or base oils for cosmetics is disclosed. The method comprises copolymerizing in the presence of an aluminum halide catalyst (i) at least one alpha-olefin having a terminal vinyl group and containing 6 to 14 carbon atoms, (ii) isobutylene and/or diisobutylene, and optionally (iii) 1-butene, coexisting in a specified ratio, and optionally hydrogenating the resulting polymer.

14 Claims, No Drawings

METHOD OF PRODUCING OLEFIN OLIGOMERS AND HYDROGENATION PRODUCTS THEREOF

BACKGROUND OF THE INVENTION

1. Field of the Invention

This invention relates to a method of producing olefin oligomers and hydrogenation products thereof. More particularly, the invention relates to a method of producing olefin oligomers or hydrogenation products thereof, which comprises feeding to the polymerization system (i) at least one alpha-olefin having a terminal vinyl group and containing 6 to 14 carbon atoms, (ii) isobutylene and/or diisobutylene, and optionally (iii) 1-butene so that the conditions $$0.25 \leq \frac{b + 2c + d}{a} \leq 4,$$
$$0 \leq \frac{d}{b + 2c} \leq 2.5 \text{ and}$$
$$0 \leq \frac{d}{a} \leq 2.5$$

wherein a is the number of moles of the alpha-olefin having a terminal vinyl group and containing 6 to 14 carbon atoms as fed to the polymerization system, b is the number of moles of isobutylene as fed to the polymerization system, c is the number of moles of diisobutylene as fed to the polymerization system and d is the number of moles of 1-butene as fed to the polymerization system, may be satisfied, while carrying out the polymerization in the presence of an aluminum halide catalyst, and optionally hydrogenating the resulting polymer.

2. Description of the Prior Art

Liquid oligomers produced from alpha-olefins each having a terminal vinyl group and containing 6 to 14 carbon atoms (such olefins hereinafter called "higher alpha-olefins"), and especially hydrogenation products thereof, thanks to their characteristic properties, are the objects of attention in respect of their use as synthetic lubricants, base oils for cosmetics and so on. The so far known methods of producing higher alpha-olefin oligomers include thermally or peroxide-initiated radical polymerization, coordinative anionic polymerization using a Ziegler catalyst (Journal of Applied Chemistry 12, 33–45(1962)), and cationic polymerization using a Lewis acid, such as boron trifluoride or an aluminum halide (U.S. Pat. No. 3,149,178), said Lewis acid being optionally modified with a ketone, an ester, an ether, an alcohol or the like (U.S. Pat. No. 3,953,361 and U.S. Pat. No. 3,952,071). Considering yield, difficulty or ease in polymerization degree regulation, breadth of molecular weight distribution, viscosity characteristics of product polymer, difficulty or ease in catalyst handling and removal and other factors collectively, those methods that employ a modified Lewis acid, especially a modified aluminum halide, as catalyst are regarded to be most advantageous among said known methods. Although aluminum halide catalysts are very preferable in view of price and easiness in handling and in other respects, polymerization of higher alpha-olefins in the presence of an aluminum halide generally tends to result in unnecessarily high polymerization degree and relatively broad molecular weight distribution. In order to overcome these disadvantages, methods using modified aluminum halide catalysts are under evaluation. However, modification of an aluminum halide with modifiers such as mentioned above causes considerable decrease in rate of polymerization of higher alpha-olefins, hence a greater amount of catalyst, a longer polymerization time and a higher polymerization temperature are required, and, as a result, the products are often of an inferior quality, containing coloring impurities, for example.

3. Detailed Description of the Invention

The present inventors have endeavored diligently to solve the above problems and produce more advantageously on a commercial scale liquid hydrocarbons useful as lubricants and base oils for cosmetics by olefin oligomerization, and have now found that a high polymerization rate results, the molecular weight of the product polymer can easily be regulated and hydrogenation of the polymerization products can be carried out effectively, if higher alpha-olefins are copolymerized with a specified amount of at least one vinylidene-type olefin selected from the group consisting of isobutylene and diisobutylene (the olefin as just defined being hereinafter called "vinylidene-type olefin" for short) or a mixture of at least one vinylidene-type olefin and 1-butene, said 1-butene also being present in a specified amount, in the presence of an aluminum halide catalyst. Thus, according to the present invention, oligomers or hydrogenation products thereof narrow in molecular weight distribution and comparable in viscosity-temperature relationship and low temperature properties to those obtained by prior art polymerization of higher alpha-olefins alone in the presence of a modified aluminum halide catalyst are produced in good yields. The hydrogenation products from the olefin oligomers produced by the method in accordance with the invention are superior in oxidation stability, especially at high temperatures, to the hydrogenation products from oligomers of higher alpha-olefins alone.

The higher alpha-olefins to be used according to the invention are, for example, 1-hexene, 4-methylpentene-1, 1-octene, 1-decene, 1-dodecene and 1-tetradecene. These higher alpha-olefins may be used each individually or in the form of a mixture of two or more of these in an arbitrary ratio. These higher alpha-olefins may contain internal olefins such as 2-pentene, 2-octene, 2-decene, 3-dodecene and so on in such amounts as have no substantial adverse effects. 1-Butene and/or the vinylidene-type olefins may also contain internal olefins such as 2-butene and so on in such amounts as have no substantial adverse effects.

According to the invention, it is important, in order to produce olefin oligomers with favorable properties at a high polymerization rate and in good yield, to feed higher alpha-olefins, vinylidene-type olefins and optionally 1-butene to the polymerization system so that the following conditions may be satisfied:

$$0.25 \leq \frac{b + 2c + d}{a} \leq 4 \quad (1)$$
$$0 \leq \frac{d}{b + 2c} \leq 2.5 \text{ and} \quad (2)$$
$$0 \leq \frac{d}{a} \leq 2.5 \quad (3)$$

where a, b, c and d are the numbers of moles of higher alpha-olefins, isobutylene, diisobutylene and 1-butene fed to the polymerization system, respectively. When the ratio (b+2c+d)/a is less than 0.25, the polymerization rate is low, the viscosity of the product is too high and the molecular weight distribution is broad, and moreover the hydrogenation product will not show substantially excellent oxidation stability, that is one feature of the invention. When, on the other hand, the ratio $(b+2c+d)/a$ is greater than 4, the polymer yield after cutting off low-boiling fractions is not good and the viscosity index of the product polymer is low. If $d/(b+2c)$ is greater than 2.5, the viscosity of the product polymer will be too high. In case $d/a$ is greater than 2.5, the polymerization rate will be low, and the product will have an unnecessarily high polymerization degree, a low viscosity index value, a high viscosity and a high pour point. It is especially preferred that $(b+2c+d)/a$ is from 0.5 to 3 and $/(b+2c)$ is from 0 to 2.0, while the above condition (3) is satisfied. By altering the ratio $d/(b+2c)$ in the range of 0 to 2.5, preferably in the range of 0 to 2.0, it is possible to control or regulate the molecular weight of the product polymer to some extent in a certain range. As understandable from the previous description, increase in the ratio $d/(b+2c)$ favors molecular weight increase, while decrease in the ratio $d/(b+2c)$ favors decrease in molecular weight. Although, in the polymerization according to the invention, the total amount of each olefin may be charged into the polymerization system all at once prior to the initiation of the polymerization, it is preferred to carry out the polymerization while feeding each olefin continuously or intermittently to the region where an aluminum halide catalyst is present and where the polymerization is going on, whereby it is possible to copolymerize a vinylidene-type olefin or a vinylidene-type olefin plus 1-butene with higher alpha-olefins especially effectively and bring about a sharper molecular weight distribution of the product polymer and besides removal of polymerization heat becomes easy.

Examples of the aluminum halide catalyst to be used in accordance with the invention are aluminum chloride, aluminum bromide, aluminum iodide and aluminum fluoride. If desired, by using in place of an aluminum halide itself a compound capable of forming an aluminum halide, it is possible to make the aluminum halide in situ. Thus, for example, a reaction mixture obtained by reacting an organoaluminum compound, such as triethylaluminum or diethylaluminum chloride, with a large excess (usually in an atomic ratio Ti/Al of from 2 to 10) of a titanium halide may be used as catalyst. Further, if desired, the aluminum halide may be modified with a variety of so-far known modifiers such as esters, ketones, alcohols and ethers. According to the invention, the polymerization with modified aluminum halide catalysts also proceeds smoothly, and it is possible to substantially decrease the amount of catalyst or shorten the polymerization time as compared with the prior art cases where higher alpha-olefins are polymerized with modified aluminum halide catalysts but with no addition of vinylidene-type olefins. Although various aluminum halide catalysts can be used as above mentioned, preferred catalysts are unmodified aluminum halides and modified aluminum chloride, and among these, unmodified aluminum chloride is most preferred in respect of catalytic activity and from cost considerations.

Desirably, the polymerization according to the invention is carried out at a temperature in the range between about 20° C. and about 120° C. A polymerization temperature in the range of from about 40° C. to about 100° C. is especially recommendable. Too low temperatures tend to cause not only heavy expenses for removal of polymerization heat but also decrease in effects of the addition of vinylidene-type olefins and as a result excessively high polymerization degrees. On the other hand, polymerization at an unnecessarily high temperature results in increase in the acid number of the reaction mixture, marked coloration of the product and decreased yield of the polymer after cutting off low-boiling fractions. The amount of the aluminum halide catalyst is preferably about 0.1 to 5 mole % based on the total monomer amount to be charged. It is preferred in commercial production to carry out the polymerization with continuous or intermittent addition of the catalyst to the polymerization system.

The polymerization may be carried out without any solvent. However, the presence of a solvent is preferable, because it lowers the viscosity of the solution and besides facilitates separation of the product from the catalyst after the reaction. Preferable solvents for the polymerization are, for example, butane, pentane, hexane, heptane, isooctane, cyclohexane, and other saturated aliphatic or alicyclic hydrocarbons. Though the amount of the solvent is not especially limited, generally it is used in an amount about 0.2 to 4 times (by volume) the total amount of monomers to be charged. In a preferred industrial embodiment of the invention, the polymerization is carried out in the copresence of an appropriate amount of a metal capable of capturing a hydrogen halide possibly formed by the action of a trace amount of water present in the polymerization system, such as aluminum, zinc, tin or lead.

After completion of the polymerization, the catalyst component is removed from the reaction mixture by filtration or centrifugation. The filtrate or liquid after the removal of the catalyst is washed with water and/or a dilute, aqueous alkali solution, the unreacted monomers and the solvent are then distilled off, and if necessary, low-boiling fractions are removed from the remaining liquid under reduced pressure. There is thus obtained a colorless to pale yellow liquid polymer. This liquid polymer as recovered from the polymerization mixture is per se useful, for example, as a synthetic lubricant. It is preferable, however, to hydrogenate said liquid polymer in order to improve its thermal and oxidation stability. In said hydrogenation, a trace amount of a halogen originating from the catalyst and unavoidably contaminating the liquid polymer after the polymerization acts as an inhibitor or poison to the hydrogenation catalyst, shortening the life thereof. It has been found by the present inventors that the life of the hydrogenation catalyst can be lengthened when the hydrogenation is carried out after washing the liquid polymer with water and/or a dilute, aqueous alkali solution and then bringing the polymer so washed into contact with an inorganic adsorbent so that the transmittance of the polymer as measured at 400 nm is not less than 0.98. The liquid polymer to be brought into contact with the inorganic adsorbent may be in the form of a solution in an appropriate solvent or in the solvent-free state. Preferably, the polymer as obtained after the removal of the $AlCl_3$-oligomer complexes from the polymerization mixture is first washed with dilute aqueous solution and then with water, and thereafter treated with the adsorbent. Improvement of the transmittance of the polymer by this treatment up to 0.98 or above means that the halogen capable of deactivating the hydrogenation catalyst has been removed to a satisfactory extent. The transmittance mentioned above is herein defined as the ratio of the intensity of the light transmitted by a liquid polymer specimen after removal of the solvent by distillation if the solvent is contained, which specimen has been taken from the liquid polymer after the treatment with the inorganic adsorbent, to the intensity of the incident beam with a wavelength of 400 nm, the cell thickness being 1 cm.

the data only for hydrogenated olefin oligomers, the corresponding olefin oligomers before hydrogenation possess almost the same properties.

Table 1

| Average molecular weight* | Viscosity at 100° F. (cSt) | Viscosity at 210° F. (cSt) | Viscosity index (VI) | Pour point (°C.) |
| --- | --- | --- | --- | --- |
| ca 400–500 | ca 20–55 | ca 5–7 | ca 90–120 | ca −45 or below |
| ca 550–650 | ca 40–100 | ca 7–11 | ca 95–120 | ca −40 or below |
| ca 650–700 | ca 70–130 | ca 10–13 | ca 100–130 | ca −30 or below |

*estimated by gel permeation chromatography (GPC)

The inorganic adsorbent suitable for achieving the above purpose is selected from among silica, silica-alumina, alumina, zeolite, diatomaceous earth, bentonite and activated clay. A mixture of two or more of these inorganic/adsorbents may also be used. The inorganic adsorbent may be in the form of a powder or be molded into granules, rods, tablets or any other appropriate form. Among these inorganic adsorbents, activated clay in the form of a powder is especially preferred in consideration of price, activity and other factors important from the commercial point of view. Contact of the liquid polymer with the inorganic adsorbent can be realized, depending upon the form of the adsorbent, by stirring a mixture of these or by allowing the polymer to pass through an adsorbent column, after adjusting the viscosity of the liquid properly, in dependence of the viscosity of the olefin polymer, by altering the temperature or by diluting with an aliphatic hydrocarbon. Generally, the amount of the inorganic adsorbent is from 1 to 20% by weight based on the liquid polymer, said amount depending on the kind of the inorganic adsorbent, for instance.

The hydrogenation can be carried out employing the methods and conditions known per se. Thus, for example, the above-mentioned liquid polymer may be brought into contact with hydrogen at a hydrogen pressure of about 2 to about 100 atmospheres and at a temperature of about 50° to about 200° C., in the presence of about 0.1 to 10% by weight based on said liquid polymer of a hydrogenation catalyst (e.g. Raney nickel, nickel on diatomaceous earth, palladium on carbon, palladium on silica, palladium on alumina) in the presence or absence of a solvent. Solvents of the same kinds usable in the polymerization mentioned above may serve also as solvents in the hydrogenation. The olefin oligomers produced by the polymerization in accordance with the present invention have properties suitable for said hydrogenation, and consequently said hydrogenation is carried out effectively. After the hydrogenation, high performance liquid hydrocarbons (hydrogenated olefin oligomers) can be obtained by removing the hydrogenation catalyst and the solvent (if present) in a conventional manner, if necessary followed by removing low-boiling fractions. Generally, the olefin oligomers and the hydrogenation products therefrom produced by the method of the invention contain hydrocarbons of 25 to 45 carbon atoms as main components, and show a pour point (according to JIS K-2269) of about −30° C. or below, a viscosity at 100° F. (according to JIS K-2283) of about 20 to about 150 cSt (centistokes), a viscosity at 210° F. (according to JIS K-2283) of about 4 to about 15 cSt, and a viscosity index (VI, according to JIS K-2284) of about 80 to about 130. The relationship between the average molecular weight and the properties can approximately be seen in Table 1 for a few typical examples. Whereas Table 1 contains The present invention that has made it possible to produce such liquid hydrocarbons with balanced, excellent properties as mentioned above easily and at low costs by oligomerization of olefins is of a great significance from the commercial viewpoint.

The invention will be further illustrated by the following examples, which are to be construed as non-limitative of the invention.

EXAMPLE 1

A system comprising a one-liter four-necked flask equipped with thermometer, stirrer, dry-ice-acetone-cooled reflux condenser, dropping funnel and glass autoclave (pressure bottle) was purged with dry nitrogen gas, and then the flask was charged with 250 ml of n-heptane and 4.0 g of anhydrous aluminum chloride. The contents were heated to 50° C. with stirring. The dropping funnel was charged with a mixture of 60 ml (479 millimoles) of 1-hexene, 49 ml (312 millimoles) of 1-octene and 39 ml (209 millimoles) of 1-decene, and the glass autoclave with a mixture of 37 g (667 millimoles) of isobutylene and 75 g (1333 millimoles) of 1-butene. When the temperature within the reactor settled at 50° C., addition of both the olefin mixtures from the dropping funnel and from the glass autoclave was commenced and continued over 1.5 hours with vigorous stirring. [(b+2c+d)/a=2.00; d/(b+2c)=2.00; d/a=1.34]. After finishing the addition of the olefins, stirring was continued for additional 1.5 hours at the same temperature. The conversion of the olefins at the moment one hour after commencement of the addition of the olefins as determined by gas chromatography was 85%. The olefin conversion at the end of the polymerization period (3 hours) as determined by gas chromatography was 97%. After the polymerization was finished, the reaction mixture was cooled, and a portion thereof was taken by decantation, the acid value of which was found to be 0.03 mg KOH/g. The color tone of the liquid reaction mixture was 0.98 when expressed in terms of the transmittance at a wavelength of 400 nm (such transmittance hereinafter called "transmittance" or short) (cell thickness=1 cm). The liquid reaction mixture was transferred to a separating funnel by decantation, washed first with two 300-ml portions of aqueous, dilute alkali solution and then with three 300-ml portions of distilled water. The n-heptane and the unreacted raw materials were removed from the organic layer by using a rotary evaporator, and 205 g of a colorless liquid polymer with a transmittance of 0.96 was obtained as a residue. This liquid polymer was heated at 180° C. under a reduced pressure of 1 mmHg for an hour to distill low-boiling fractions off. The remaining, colorless liquid polymer weighed 180 grams, the yield of the remaining liquid after cutting low-boiling fractions off, based on the total amount of the olefins converted (such yield hereinafter called "yield of the residue after cutting") thus being 88%. The pour point, viscosity at 100° F., viscosity at 210° F. and viscosity index (VI) of the residual liquid after cutting low-boiling fractions off were measured and found to be −40° C., 77.58 cSt, 9.17 cSt and 102, respectively. Subsequently, the above low-boiling-fraction-cut, liquid polymer (160 g), 200 ml of n-heptane and 5.5 g of Raney nickel were placed in a 1000-ml autoclave having an outlet for sampling and equipped with a magnetic stirrer. After sufficient replacement of the gas within the autoclave with hydrogen gas, the temperature was raised to 125° C. and the hydrogenation carried out with stirring at a hydrogen pressure of 10 atmospheres for 7 hours. An hour after the charging of hydrogen under pressure, sampling was made through said outlet for sampling. The degree of hydrogenation in an hour as calculated from the bromine number was 31%. After cooling the autoclave to room temperature, the hydrogen was discharged, the contents were taken out, and the catalyst was filtered off. The n-heptane was distilled off from the filtrate by using a rotary evaporator. The pour point, viscosity at 100° F., viscosity at 210° F. and viscosity index of the colorless residual liquid were −40° C., 78.75 cSt (100° F.), 9.21 cSt (210° F.) and 101 (VI), respectively. A test for distillation of oligomers was made with this hydrogenated liquid polymer in a reduced pressure distillation apparatus. The average molecular weight of each fraction was determined by gel permeation chromatography (GPC). The distillation test gave the following results: lower than $C_{24}=3\%$, $C_{24}$ to $C_{30}=11\%$, $C_{30}$ to $C_{35}=17\%$, $C_{35}$ to $C_{40}=27\%$, $C_{40}$ to $C_{45}=20\%$ and higher than $C_{45}=22\%$ by weight.

As is clear from the above results, the liquid polymer produced by this polymerization shows a sharp molecular weight distribution and is excellent in said various properties.

EXAMPLE 2

The same reaction apparatus as in Example 1 was used. The monomers charged were 37 ml (300 millimoles) of 1-hexene, 93 ml (600 millimoles) of 1-octene, 113 ml (600 millimoles) of 1-decene, 42 g (750 millimoles) of isobutylene and 42 g (750 millimoles) of 1-butene. The polymerization was carried out for 3 hours by proceeding as in Example 1 except that the polymerization temperature was 70° C. [$(b+2c+d)/a=1.00$; $d/(b+2c)=1.00$; $d/a=0.50$].

The final olefin conversion was 97%. The liquid polymerization mixture as separated from the polymerization mixture by decantation showed an acid value of 0.08 mg KOH/g and a transmittance of 0.65. The reaction mixture was transferred to a separating funnel, and washed with an aqueous, dilute alkali solution and distilled water as in Example 1. Removal of the n-heptane and the unreacted raw materials from the organic layer by distillation in a rotary evaporator gave 245 g of a colorless liquid polymer with a transmittance of 0.95 as a residue. The same autoclave as used in Example 1 was charged with 200 g of this liquid polymer, 200 ml of n-heptane and 6.0 g of a 5% Pd-carbon catalyst, and the hydrogenation was carried out at a temperature of 150° C. and at a hydrogen pressure of 10 atmospheres for 7 hours. The catalyst was then filtered off, and the n-heptane distilled off from the filtrate in a rotary evaporator. The residual liquid was transferred to a reduced pressure distillation apparatus, and low-boiling fractions were removed by thermal treatment under conditions of 1 mm Hg and 180° C. for an hour. The residue after cutting off of low-boiling fractions weighed 170 grams. The pour point, viscosity at 100° F., viscosity at 210° F. and viscosity index of said residue were −50° C., 53.09 cSt (100° F.), 7.50 cSt (210° F.) and 112 (VI), respectively. A distillation test was made for said residue in a manner similar to that in Example 1. The results of the distillation test were as follows (% by weight): lower than $C_{24}=2\%$, $C_{24}$ to $C_{30}=15\%$, $C_{30}$ to $C_{35}=22\%$, $C_{35}$ to $C_{40}=28\%$, $C_{40}$ to $C_{45}=16\%$ and higher than $C_{45}=17\%$.

EXAMPLE 3

The same reaction apparatus as in Example 1 was charged with 250 ml of n-hexane, 156 ml (1000 millimoles) of 1-octene and 4.0 g of anhydrous aluminum chloride, and the temperature of the contents was raised to 50° C. by warming. Thereafter, a mixture of 90 g (800 millimoles) of diisobutylene, 22 g (400 millimoles) of 1-butene and 45 g (800 millimoles) of isobutylene was added continuously from the glass autoclave with vigorous stirring over 1.5 hours. [$(b+2c+d)/a=2.80$, $d/(b+2c)=0.17$, $d/a=0.40$]. Since the heat of polymerization caused a temperature rise, cooling and heating were repeated so as to maintain the temperature of the flask contents at a constant value of 50° C. After the addition of the mixture of diisobutylene, 1-butene and isobutylene was finished, stirring was continued for additional 1.5 hours at the same temperature. The olefin conversion after the polymerization amounted to 99%. The acid value and transmittance of the liquid polymerization mixture were 0.03 mg KOH/g and 0.98, respectively. The liquid polymerization mixture was treated as in Example 1 to give 261 g of a colorless liquid polymer with a transmittance of 0.98. An autoclave was charged with 200 g of this liquid polymer, 250 ml of n-heptane and 6.0 g of Raney nickel, and the hydrogenation was carried out at a hydrogen pressure of 10 atmospheres and at a temperature of 125° C. for 7 hours. The residual liquid obtained after thermal treatment under conditions of 1 mm Hg and 180° C. for an hour weighed 142 grams, and the pour point, viscosity at 100° F., viscosity at 210° F. and viscosity index of this residual liquid were −52° C., 40.21 cSt(100° F.), 5.82 cSt(210° F.) and 93 (VI), respectively.

EXAMPLE 4

The same polymerization apparatus as in Example 1 was charged with 250 ml of n-hexane, 75 ml (600 millimoles) of 1-hexene, 124 ml (800 millimoles) of 1-octene, 113 ml (600 millimoles) of 1-decene, 8.0 g of aluminum bromide, 11 g (200 millimoles) of 1-butene, 11 g (200 millimoles) of isobutylene and 67 g (600 millimoles) of diisobutylene, and the polymerization was carried out at 40° C. for 5 hours with vigorous stirring. [$(b+2c+d)/a=0.80$, $d/(b+2c)=0.14$, $d/a=0.10$]. Since the heat of polymerization caused a temperature rise, the temperature of the flask contents was maintained at a constant value of 40° C. by cooling using a dry-ice-acetone bath. The whole amount of then liquid polymer obtained after the polymerization was hydrogenated in accordance with the manner of Example 2, giving 297 g of a colorless liquid polymer. When low-boiling fractions were cut off by thermal treatment of 200 g of this liquid polymer under conditions of 1 mm Hg and 180° C. for an hour, there was obtained 172 g of a residual liquid. The pour point, viscosity at 100° F., viscosity at 210° F. and viscosity index (VI) of this residual liquid were −55° C., 42.87 cSt, 6.73 cSt and 120, respectively.

EXAMPLE 5

The same reaction apparatus as in Example 1 was charged with 1 g of metallic aluminum, 8.0 g of anhydrous aluminum chloride and 3.96 g of ethylene glycol diacetate, and the catalyst was matured by stirring in a nitrogen atmosphere at 100° C. for 3 hours. Thereafter, 250 ml of n-heptane was added, and the temperature of the contents was adjusted to 75° C. The dropping funnel was charged with a mixture of 62 ml (500 millimoles) of 1-hexene, 78 ml (500 millimoles) of 1-octene, 94 ml (500 millimoles) of 1-decene and 50 ml (240 millimoles) of 1-dodecene, while the glass autoclave was charged with a mixture of 17 g (300 millimoles) of 1-butene and 67 g (1200 millimoles) of isobutylene. The both olefin mixtures were added continuously over 3 hours with vigorous stirring in the same manner as in Example 1. [(b+2c+d)/a=0.86, d/(b+2c)=0.25, d/a=0.17]. After the addition was finished, stirring was continued for further 3 hours at the same temperature (75° C.). The conversion of the olefins was 93%. The liquid polymerization mixture was treated as in Example 2 to produce a hydrogenated liquid polymer. When this was subjected to thermal treatment under conditions of 1 mm Hg and 180° C. for an hour, the yield of the residue after cutting was 84%. The average molecular weight, pour point, viscosity at 100° F., viscosity at 210° F. and viscosity index of the residual liquid (hydrogenated liquid polymer) were 495 (measured by GPC), −60° C., 30.85 cSt (100° F.), 5.45 cSt (210° F.) and 124 (VI), respectively.

EXAMPLES 6 TO 8

Hydrogenated liquid polymers were prepared by using the same apparatus as in Example 1 and proceeding as in Example 2, under the polymerization conditions, such as composition of monomers to be charged, manner in which the monomers were added, polymerization temperature and catalyst, being varied. The results are summarized in Table 2 and Table 3. In each example, the solvent for polymerization (250 ml) and the solvent for hydrogenation (75 to 125% by volume based on the liquid polymer) were of the same kind, that is n-hexane in Example 6, n-heptane in Example 7 and cyclohexane in Example 8. The hydrogenation catalyst was Raney nickel (in Example 6), 5% Pd-carbon (in Example 7) or 3% Pd-silica (in Example 8). In each example, the amount of the catalyst was 3 to 5 percent by weight based on the polymer to be reduced (200 g). The hydrogenation conditions employed were hydrogen pressure of 10 atmospheres, reaction temperature of 125° C. and reaction time of 7 hours. In each case, low-boiling fractions were cut off under conditions of 1 mm Hg, 180° C. and an hour. The average molecular weight values appearing in Table 3 were determined by GPC.

Table 2

| Example | Higher alpha-olefins (g) | 1-Butene (g) | Vinylidene-type olefin (g) | $\dfrac{b+2c+d}{a}$ | $\dfrac{d}{b+2c}$ | $\dfrac{d}{a}$ | Monomer addition | Polymerization temperature (°C.) | Polymerization time (hrs) | Polymerization catalyst (g) |
|---|---|---|---|---|---|---|---|---|---|---|
| 6 | 1-octene 53 1-decene 74 | 46 | isobutylene 66 | 2.00 | 0.69 | 0.82 | as in Example 1 | 50 | 4.0 | AlCl$_3$ 4.0 |
| 7 | 1-octene 190 | 43 | isobutylene 29 | 0.76 | 1.48 | 0.45 | as in Example 1 | 45 | 3.0 | AlBr$_3$ 8.0 |
| 8 | 1-hexene 47 1-octene 87 1-decene 93 | 0 | diisobutylene 112 | 0.50 | 0.00 | 0.00 | as in Example 3 | 50 | 3.0 | AlCl$_3$ 4.0 |

Table 3

| Example | Olefin conversion (%) | Acid value (mg KOH/g) | Transmittance After polymerization | Transmittance After alkali washing and solvent removal | Yield of residue after cutting (%) | Average molecular weight | Pour point (°C.) | Viscosity (cst) 100° F. | Viscosity (cst) 210° F. | Viscosity index (VI) |
|---|---|---|---|---|---|---|---|---|---|---|
| 6 | 95 | 0.03 | 0.98 | 0.96 | 86 | 665 | −50 | 84.62 | 10.23 | 110 |
| 7 | 98 | 0.25 | 0.77 | 0.93 | 90 | 700 | −42 | 103.63 | 12.35 | 116 |
| 8 | 97 | 0.05 | 0.98 | 0.96 | 77 | 495 | −55 | 42.91 | 6.47 | 111 |

EXAMPLE 9

The same reaction apparatus as in Example 1 was charged with 200 ml of n-heptane and 1.34 g of anhydrous aluminum chloride, and the contents were heated to 75° C. The dropping funnel was charged with a mixture of 90 ml (715 millimoles) of 1-hexene, 75 ml (475 millimoles) of 1-octene and 60 ml (310 millimoles) of 1-decene, and the glass autoclave with a mixture of 84 g (1500 millimoles) of isobutylene and 84 g (1500 millimoles) of 1-butene. [(b+2c+d)/a=2.00, d/(b+2c)=1.00, d/a=1.00]. Both the olefin mixtures were added continuously from the dropping funnel and the glass autoclave with vigorous stirring at a constant flask temperature of 75° C. at such a rate that the addition was complete in 5 hours. At two hours and four hours after commencement of the olefin addition, each 1.34 g of anhydrous aluminum chloride was supplemented. After completion of the olefin addition, stirring was continued for additional 30 minutes at the same temperature. The conversion of the olefins after the reaction was 97%, the acid value of the liquid reaction mixture was 0.10 mg KOH/g. The liquid reaction mixture was washed with aqueous dilute alkali solution and with distilled water in accordance with the corresponding procedure in Example 1. When the n-heptane and the unreacted olefins were distilled off from the organic layer in a rotary evaporator, there was obtained 290 g of a pale yellow liquid polymer. This liquid polymer (240 g) was subjected to hydrogenation as in Example 2. After removal of the catalyst and the solvent, low-boiling fractions were cut off under conditions of 1 mm Hg and 180° C. The yield of the residue after cutting was 77%. The pour point, viscosity at 100° F., viscosity at 210° F., viscosity index and average molecular weight of the hydrogenated liquid polymer so produced were $-47.5°$ C., 49.49 cSt, 6.67 cSt, 95 (VI) and 530 (determined by GPC), respectively.

EXAMPLE FOR COMPARISON—1

The same reaction apparatus as in Example 1 was charged with 250 ml of n-heptane, 180 ml (1438 millimoles) of 1-hexene, 146 ml (938 millimoles) of 1-octene, 118 ml (624 millimoles) of 1-decene and 4.0 g of anhydrous aluminum chloride, and the polymerization was effected at 95° C. with vigorous stirring for 5 hours. The conversion of the olefins after 5 hours was 95%. After cooling to room temperature, a portion of the liquid polymerization mixture was taken out by decantation, and the acid value and the transmittance were measured as in Example 1 and found to be 1.35 mg KOH/g and 0.00, respectively. The transmittance after the n-heptane was distilled off was 0.80. The liquid reaction mixture was treated as in Example 1 to give 290 g of a yellow liquid polymer with a transmittance of 0.80. An autoclave was charged with 160 g of this liquid polymer, 200 ml of n-heptane and 5.5 g of Raney nickel, and the hydrogenation was carried out at 125° C. and at a hydrogen pressure of 10 atmospheres for 20 hours. One hour after commencement of the hydrogenation, sampling was made through the outlet for sampling. The degree of hydrogenation in one hour determined from the bromine number was 15%. The contents were taken out, and the catalyst was filtered off. The n-heptane was distilled off from the filtrate in a rotary evaporator, and then low-boiling fractions were cut off by treatment at 1 mm Hg and 180° C. for an hour. The yield of the residue after cutting was 92%. The pour point, viscosity at 100° F., viscosity at 210° F. and viscosity index of the residual liquid after cutting off of low-boiling fractions were $-35°$ C., 113.90 cSt (100° F.), 13.82 cSt (210° F.) and 121 (VI), respectively. The distillation test on said residual liquid gave the following results: lower than $C_{24}=2\%$, $C_{24}$ to $C_{30}=6\%$, $C_{30}$ to $C_{35}=6\%$, $C_{35}$ to $C_{40}=10\%$, $C_{40}$ to $C_{45}=15\%$ and higher than $C_{45}=61\%$ (by weight).

When the above results are compared with those in Example 1, the characteristic features of the method according to the present invention can clearly be understood. Namely, in accordance with the invention, the polymerization reaction proceeds smoothly in spite of the fact that the polymerization is carried out under rather mild conditions, and the liquor polymer produced can easily be hydrogenated and moreover a sharp molecular weight distribution results.

EXAMPLE FOR COMPARISON—2

The same reaction apparatus as in Example 1 was charged with 0.7 g of metallic aluminum, 6.7 g of anhydrous aluminum chloride and 3.65 g of ethylene glycol diacetate, and the catalyst was matured by stirring at 100° C. for 3 hours. Thereafter, 250 ml of n-heptane, 150 ml (1200 millimoles) of 1-hexene, 124 ml (800 millimoles) of 1-octene, 113 ml (600 millimoles) of 1-decene and 89 ml (400 millimoles) of 1-dodecene were added, and the polymerization was effected at 95° C. for 20 hours with vigorous stirring. The conversion of the olefins in an hour was as low as 5%.

The acid value and the transmittance of the liquid polymerization mixture were 1.75 mg KOH/g and 0.00, respectively. After thoroughly washing the liquid polymerization mixture with an aqueous dilute alkali solution and with distilled water, the n-heptane and the unreacted raw materials were distilled off in a rotary evaporator. There was obtained as a residue 297 g of a yellow liquid polymer showing a transmittance of 0.94. An autoclave was charged with 160 g of this liquid polymer, 200 ml of n-heptane and 5.5 g of Raney nickel. The hydrogenation was carried out at a temperature of 125° C. and at a hydrogen pressure of 10 atmospheres for 20 hours. After filtering the catalyst off, the solvent was distilled off from the filtrate, and then low-boiling fractions were cut off by treatment at 180° C. under 1 mm Hg for an hour. The yield of the residue after cutting was 83%. The pour point, viscosity at 100° F., viscosity at 210° F. and viscosity index of the colorless liquid left after cutting off of low-boiling fractions were $-65°$ C., 22.68 cSt, 4.45 cSt and 123 (VI), respectively.

The average molecular weight of said residual liquid after the cutting as measured by GPC was 422. The above results indicate that the average molecular weight is shifted to the lower molecular weight region if a modified aluminum chloride catalyst is used, but that instead disadvantages are encountered, such as decrease in catalytic activity, requirement of a larger amount of catalyst and of a longer polymerization period, hence increase in the acid value of the liquid polymerization mixture.

EXAMPLE FOR COMPARISON—3

The same reaction apparatus as in Example 1 was charged with 250 ml of n-hexane and 4.0 g of anhydrous aluminum chloride. The dropping funnel was charged with 37 ml (300 millimoles) of 1-hexene, 93 ml (600 millimoles) of 1-octene and 113 ml (600 millimoles) of 1-decene, and the glass autoclave with 84 g (1500 millimoles) of 1-butene alone. The temperature of the polymerization reactor was raised to 50° C., and the above olefins were added continuously over 3 hours with vigorous stirring. After completion of the addition, stirring was continued for additional 5 hours at the same temperature (50° C.). The conversion of the olefins was 93%. A hydrogenated liquid polymer (240 g) was obtained by treating the liquid polymerization mixture by the procedure described in Example 2. The pour point, viscosity at 100° F., viscosity at 210° F., viscosity index and average molecular weight of the residue after low-boiling-fraction cutting by treatment at 1 mm Hg and at 180° C. for an hour (the yield of the residue after cutting being 90%) were −30° C., 169.11 cSt, 17.46 cSt, 115 (VI) and 1250 (by GPC), respectively.

EXAMPLE FOR COMPARISON—4

The same reaction apparatus as in Example 1 was charged with 250 ml of n-heptane and 4.0 g of anhydrous aluminum chloride. The dropping funnel was charged with a liquid mixture of 13 ml (100 millimoles) of 1-hexene, 31 ml (200 millimoles) of 1-octene and 19 ml (100 millimoles) of 1-decene, and the glass autoclave with a mixture of 56 g (1000 millimoles) of 1-butene and 90 g (1600 millimoles) of isobutylene. The above olefins were added to the reaction apparatus continuously over 2 hours, the polymerization temperature being 50° C. After completion of the olefin addition, stirring was continued for further 2 hours at the same temperature. The conversion of the olefins was 98%. Treatment of the liquid polymerization mixture in the same manner as in Example 2 gave 185 g of a hydrogenated liquid polymer. Low-boiling fractions were cut off by treatment at 1 mm Hg and at 180° C. for an hour. The yield of the residue after cutting was 42%. The pour point, viscosity at 100° F., viscosity at 210° F., viscosity index and average molecular weight of the residual liquid after low-boiling fraction cutting were −25° C., 101.33 cSt, 8.85 cSt, 53 (VI) and 475 (by GPC), respectively.

Thus, in a case where 1-butene and isobutylene are used in large excesses against higher alpha-olefins, the yield of the residue after cutting is markedly decreased, and at the same time the viscosity characteristics of the liquid polymer produced are remarkably worsened.

OXIDATION STABILITY TESTS

An oxidation stability test was carried out on the hydrogenated polymer produced in Example 1 (Sample No. I), the hydrogenated polymer produced in Example 2 (Sample No. II), the hydrogenated liquid polymer produced in Example 6 (Sample No. III), the hydrogenated polymer produced in Example 9 (Sample No. IV), the hydrogenated polymer produced in Example for Comparison—1 (Sample No. V), a fraction (Sample No. VI) boiling at from 150° to 260° C. under 0.1 mm Hg that was obtained by distillation of the hydrogenated polymer produced in Example for Comparison—1, a fraction (Sample No. VII) boiling at from 100° to 265° C. under 0.1 mm Hg that was obtained from a commercially available mineral oil lubricant by distillation following separation of additives contained therein by column chromatography, and a fraction (Sample No. VIII) boiling at from 120° to 250° C. under 0.1 mm Hg that was prepared by polymerizing 1-decene at 10° C. using a catalyst of the $BF_3$/isobutyric acid complex-$BF_3$ type, followed by washing with water, hydrogenation and distillation. The test was performed essentially in accordance with the Indiana stirring method (JIS K 2514). Thus, a 300-ml four-necked flask equipped with stirrer, reflux condenser, air inlet and thermometer was charged with 120 g of each sample, 5.0 g of iron pieces and 5.0 g of copper pieces, and the test was carried out in an oil bath maintained at 165°±1° C. at a rate of air flow of 10 liters per hour and at 1000 revolutions per minute. Sampling was made each 12 hours, and the change of the viscosity at 100° F. and of the acid value (mg KOH/g) in dependence of time was followed. Some test results are shown in Table 4.

Table 4

| Sample No. | Viscosity at 210° F. (cSt) | After 36 hours of air blowing | | After 60 hours of air blowing | |
|---|---|---|---|---|---|
| | | Viscosity ratio[a] | Increase in acid value[b] | Viscosity ratio[a] | Increase in acid value[b] |
| I | 9.21 | 1.74 | 4.71 | 3.56 | 10.33 |
| II | 7.50 | 1.75 | 4.78 | 3.38 | 11.25 |
| III | 10.23 | 1.76 | 4.69 | 3.47 | 9.83 |
| IV | 6.67 | 1.74 | 4.71 | 3.00 | 8.72 |
| V | 13.82 | 1.95 | 7.40 | 5.21 | 14.60 |
| VI | 6.91 | 1.78 | 6.48 | 4.11 | 13.05 |
| VII | 6.51 | 3.38 | 15.76 | 17.24 | |
| VIII | 5.09 | 2.01 | 6.99 | 4.66 | 13.81 |

Notes:
[a]Viscosity ratio =
$$\frac{\text{Viscosity of the sample at 100° F. after a specified period of air blowing (cSt)}}{\text{Viscosity of the sample at 100° F. before the test (cSt)}}$$
[b]Increase in acid value = [acid value of the sample after a specified period of air blowing (mg KOH/g)] − [acid value of the sample before the test (mg KOH/g)]

It is clear from Table 4 that the hydrogenated liquid polymers produced in accordance with the invention are superior in oxidation stability to other hydrocarbon lubricant base oils.

Another oxidation stability test was carried out on the hydrogenated polymer produced in Example 9 (Sample No. IV), the fraction (Sample NO. VI) boiling at from 150° to 260° C. under 0.1 mm Hg that was prepared by distillation of the hydrogenated polymer produced in Example for Comparison—1, and the fraction (Sample No. VII) boiling at from 100° to 265° C. under 0.1 mm Hg that was prepared from the commercial mineral oil lubricant mentioned above by distillation following separation of additives contained therein by column chromatography. The test was performed by the same method and under the same conditions as in the previously mentioned test, except that 0.1% by weight of zinc di-n-butyldithiocarbamate was added as an antioxidant and that the oil bath temperature was maintained at 190°±1° C., in order to examine the effect of said antioxidant on the oxidation stability. The results are shown in Table 5.

Table 5

| Sample No. | Oxidation period* (hrs) | 10 | 15 | 20 | 25 | 30 | 35 | 40 | 45 |
|---|---|---|---|---|---|---|---|---|---|
| IV | Viscosity ratio** | | | | 1.0 | 1.0 | 1.09 | 1.33 | 1.72 |
| | Increase in acid value*** | | | | 0.0 | 0.0 | 0.25 | 1.15 | 2.38 |
| VI | Viscosity ratio** | | 1.0 | 1.0 | 1.13 | 1.25 | 1.38 | 1.55 | 1.96 |
| | Increase in acid value*** | | 0.0 | 0.0 | 0.60 | 1.35 | 2.30 | 3.55 | 5.40 |
| VII | Viscosity ratio** | 1.08 | 1.25 | 1.46 | 1.80 | | | | |
| | Increase in acid | 0.50 | 1.71 | 3.35 | 6.50 | | | | |

Table 5-continued

| Sample No. | Oxidation period* (hrs) value*** | 10 | 15 | 20 | 25 | 30 | 35 | 40 | 45 |
|---|---|---|---|---|---|---|---|---|---|

*The same as air blowing period.
**See Note (a) to Table 4.
***See Note (b) to Table 4

EXAMPLE 10

A one-liter four-necked flask equipped with thermometer, stirrer, reflux condenser and dropping funnel was charged with 160 ml of n-heptane and 1.5 g of anhydrous aluminum chloride, and the contents were maintained at a temperature of 75° to 80° C. by heating with stirring. The dropping funnel was charged with a mixture of 62 ml (500 millimoles) of 1-hexene, 52 ml (335 millimiles) of 1-octane and 42 ml (220 millimoles), while the glass autoclave was charged with a mixture of 73 g (1310 millimoles) of isobutylene and 37 g (655 millimoles) of 1-butene. The olefin mixtures were added continuously from the dropping funnel and the glass autoclave over 3 hours to effect the polymerization $[(b+2c+d)/a=1.87, d/(b+2c)=0.50, d/a=0.62]$. After finishing the polymerization and cooling the flask contents to room temperature, the liquid polymerization mixture was transferred to a 2-liter separating funnel by decantation under separation of the catalyst that had precipitated. The mixture was washed with two 500-ml portions of aqueous 0.5 N NaOH solution and then with two 500-ml portions of distilled water. The n-heptane was distilled off from the organic layer under reduced pressure. The average molecular weight of the liquid polymer (residual liquid) as determined by gel permeation chromatography (GPC) was 350, and the tramsmittance at 400 nm (cell thickness=1 cm) was 0.955. The total amount of the liquid polymer prepared by four repetitions of the above procedure finally weighed 850 grams. This liquid polymer (400 g) and 32 g of powdery activated clay were charged into a flask, stirred vigorously at room temperature for 60 minutes, and then filtered. The transmittance at 400 nm of the liquid polymer was improved to 0.997 by this activated clay treatment. A 300-ml autoclave with a magnetic stirrer was charged with 75 g of the liquid polymer so treated with activated clay, 75 ml of n-heptane and 1.125 g of a nickel/diatomaceous earth catalyst with a nickel content of 55%, and the hydrogenation was effected at a hydrogen pressure of 30 atmospheres and at a temperature of 200° C. with stirring for 2 hours. The degree of hydrogenation at the end of the hydrogenation (i.e. after 2 hours) was estimated to be 94% on the basis of the result of a surviving double bond determination (bromine number). After the 2-hour reaction, the autoclave was cooled to room temperature, and then the liquid reaction mixture (150 ml) was taken out with care by the use of the outlet for sampling. The liquid reaction mixture so taken out apparently did not contain any trace of the catalyst. The autoclave was charged again with 70 g of the liquid polymer after the treatment with activated clay and 70 ml of n-heptane, and a second run of the hydrogenation was carried out at a hydrogen pressure of 30 atmospheres and at a temperature of 200° C. with stirring for 2 hours. After the reaction, the autoclave was cooled to room temperature and the liquid reaction mixture (150 ml) was taken out via the outlet for sampling with care in a manner similar to that previously described. The degree of hydrogenation in this second run was 94%. Further three runs of the hydrogenation were repeated by a similar procedure and under similar conditions. The degree of hydrogenation for the fifth run was 78%.

EXAMPLE 11

The same procedure as in Example 10 was repeated, except that 400 g of the liquid polymer after the removal of n-heptane by distillation was treated with 16 g of powdery activated clay, that 2.250 g of a palladium-alumina catalyst with a palladium content of 0.3% was used in place of the 1.125 g of the nickel-diatomaceous earth catalyst, and that the hydrogenation temperature was 180° C. The results are shown in Table 6.

EXAMPLES 12 AND 13

The same reaction apparatus as in Example 10 was charged with 160 ml of n-heptane and 1.0 g of anhydrous aluminum chloride, and the contents were heated to 75° C. with stirring. The dropping funnel was charged with a liquid mixture consisting of 25 ml (187 millimoles) of 1-hexene, 60 ml (374 millimoles) of 1-octene and 70 ml (374 millimoles) of 1-decene, and the glass autoclave with 28 g (491 millimoles) of isobutylene and 28 g (491 millimoles) of 1-butene. Both the olefin mixtures were added continuously over 3 hours in the same manner as in Example 10. $[(b+2c+d)/a=1.05, d/(b+2c)=1.00, d/a=0.53]$. The liquid polymerization mixture was treated in the same manner as in Example 10, to give a liquid polymer. The average molecular weight of this polymer as measured by gel permeation chromatography (GPC) was 400. Five repetitions of the above procedure finally gave 805 grams of the liquid polymer. Two kinds of samples for hydrogenation were prepared by treating this liquid polymer with the inorganic adsorbents shown in Table 6. The hydrogenation was carried out, as in Example 10, in an autoclave using 75 ml of n-heptane. In the case where a nickel-diatomaceous earth catalyst with a nickel content of 55% was used for the hydrogenation, the reaction temperature was 200° C. and the reaction time was 2 hours. In the case where a palladium-alumina catalyst with a palladium content of 0.3% was used, the reaction temperature was 180° C. and the reaction time was 2 hours. In each example, five repeated runs were carried out by a procedure similar to that in Example 10. The hydrogenation degree values for the first, second and fifth runs in each experiment as attained by changing the kind of liquid polymer, the kind of inorganic adsorbent and the hydrogenation catalyst and repeating the hydrogenation are summarized in Table 6.

Table 6

| Example No. | Liquid polymer Transmittance | Inorganic adsorbent Kind | Weight % | Transmittance after treatment | Hydrogenation catalyst Kind | Weight % based on polymer | Hydrogen pressure (atms) | Temperature (°C.) | Degree of hydrogenation 1st time | 2nd time | 5th time |
|---|---|---|---|---|---|---|---|---|---|---|---|
| 11 | 0.955 | Activated clay | 4 | 0.985 | Palladium on alumina | 3.0 | 30 | 180 | 93 | 94 | 81 |
| 12 | 0.962 | Alumina | 10 | 0.996 | Nickel on diatomaceous earch | 1.5 | 30 | 200 | 94 | 93 | 77 |
| 13 | 0.962 | Diatomaceous earch | 7 | 0.988 | Palladium on alumina | 3.0 | 30 | 180 | 93 | 94 | 83 |

What is claimed is:

1. A method of producing an olefin oligomer, which comprises feeding to the polymerization system (i) at least one alpha-olefin having a terminal vinyl group and containing 6 to 14 carbon atoms, (ii) isobutylene and/or diisobutylene, and optionally (iii) 1-butene so that the conditions $$0.25 \leq \frac{b + 2c + d}{a} \leq 4,$$
$$0 \leq \frac{d}{b + 2c} \leq 2.5 \text{ and}$$
$$0 \leq \frac{d}{a} \leq 2.5$$

wherein a is the number of moles of the alpha-olefin having a terminal vinyl group and containing 6 to 14 carbon atoms as fed to the polymerization system, b is the number of moles of isobutylene as fed to the polymerization system, c is the number of moles of diisobutylene as fed to the polymerization system and d is the number of moles of 1-butene as fed to the polymerization system, may be satisfied, while carrying out the polymerization in the presence of an aluminum halide catalyst.

2. A method as claimed in claim 1, wherein said aluminum halide catalyst is aluminum chloride, aluminum bromide, aluminum iodide, aluminum fluoride, an aluminum halide prepared by reacting an organoaluminum compound with a titanium halide in a Ti/Al atomic ratio of from 2 to 10, or a modified aluminum halide, the modifier being an ester, a ketone, an alcohol, an ether or the like.

3. A method as claimed in claim 2, wherein said aluminum halide catalyst is aluminum chloride.

4. A method as claimed in claim 1, wherein (b+2c+d)/a amounts to from 0.5 to 3 and d/(b+2c) to from 0 to 2.0.

5. A method as claimed in claim 1, wherein the polymerization is carried out at a temperature in the range of 20° C. to 120° C.

6. A method as claimed in claim 5, wherein the polymerization is carried out at a temperature in the range of 40° C. to 100° C.

7. A method as claimed in claim 1, wherein the polymerization is carried out in the presence of a solvent.

8. A method as claimed in claim 7, wherein said solvent for the polymerization is a saturated aliphatic or alicyclic hydrocarbon.

9. A method as claimed in claim 8, wherein said saturated aliphatic or alicyclic hydrocarbon is butane, pentane, hexane, heptane, isooctane or cyclohexane.

10. A method of producing a hydrogenated olefin oligomer, which comprises feeding to the polymerization system (i) at least one alpha-olefin having a terminal vinyl group and containing 6 to 14 carbon atoms, (ii) isobutylene and/or diisobutylene, and optionally (iii) 1-butene so that the conditions $$0.25 \leq \frac{b + 2c + d}{a} \leq 4,$$
$$0 \leq \frac{b + 2c}{a} \leq 2.5 \text{ and}$$
$$0 \leq \frac{d}{a} \leq 2.5$$

wherein a is the number of moles of the alpha-olefin having a terminal vinyl group and containing 6 to 14 carbon atoms as fed to the polymerization system, b is the number of moles of isobutylene as fed to the polymerization system, c is the number of moles of diisobutylene as fed to the polymerization system and d is the number of moles of 1-butene as fed to the polymerization system, may be satisfied, while carrying out the polymerization in the presence of an aluminum halide catalyst, and hydrogenating the resulting polymer.

11. A method as claimed in claim 10, wherein the resulting polymer is washed with water and/or a dilute, aqueous alkali solution, brought into contact with an inorganic adsorbent so that the transmittance of the polymer as measured in the solvent-free state at 400 nm is not less than 0.98, and then hydrogenated.

12. A method as claimed in claim 11, wherein said inorganic adsorbent is silica, silica-alumina, alumina, zeolite, diatomaceous earth, bentonite or activated clay, or a mixture of these.

13. A method as claimed in claim 11, wherein said inorganic adsorbent is used in an amount of 1 to 20% by weight based on the polymer to be treated therewith.

14. A method as claimed in claim 10, wherein the hydrogenation is carried out at a temperature of 50° C. to 200° C. and at a hydrogen pressure of 2 to 100 atmospheres in the presence of a hydrogenation catalyst.

* * * * *